(12) United States Patent
Lim

(10) Patent No.: US 10,058,496 B2
(45) Date of Patent: Aug. 28, 2018

(54) THERMOSENSITIVE IONIC COMPOSITE, PREPARING METHOD THEREOF, AND BIODEGRADABLE COMPOSITION CONTAINING THE SAME

(71) Applicant: RESEARCH & BUSINESS FOUNDATION SUNGKYUNKWAN UNIVERSITY, Suwon-si (KR)

(72) Inventor: Yong Taik Lim, Seongnam-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 196 days.

(21) Appl. No.: 14/828,876

(22) Filed: Aug. 18, 2015

(65) Prior Publication Data

US 2016/0046809 A1     Feb. 18, 2016

(30) Foreign Application Priority Data

Aug. 18, 2014  (KR) ........................ 10-2014-0107045

(51) Int. Cl.

| | |
|---|---|
| *A61K 8/65* | (2006.01) |
| *A61K 47/34* | (2017.01) |
| *A61K 47/36* | (2006.01) |
| *A61K 8/88* | (2006.01) |
| *A61K 8/73* | (2006.01) |
| *A61K 47/42* | (2017.01) |
| *A61Q 19/00* | (2006.01) |
| *A61K 8/04* | (2006.01) |
| *A61K 8/00* | (2006.01) |
| *C08L 89/04* | (2006.01) |
| *C08L 89/06* | (2006.01) |
| *A61K 47/38* | (2006.01) |
| *A61K 9/00* | (2006.01) |

(52) U.S. Cl.
CPC ................ *A61K 8/65* (2013.01); *A61K 8/042* (2013.01); *A61K 8/731* (2013.01); *A61K 8/735* (2013.01); *A61K 8/88* (2013.01); *A61K 9/0014* (2013.01); *A61K 9/0024* (2013.01); *A61K 47/34* (2013.01); *A61K 47/36* (2013.01); *A61K 47/38* (2013.01); *A61K 47/42* (2013.01); *A61Q 19/00* (2013.01); *C08L 89/04* (2013.01); *C08L 89/06* (2013.01); *A61K 2800/242* (2013.01); *A61K 2800/5424* (2013.01)

(58) Field of Classification Search
CPC .......... A61K 8/65; A61K 8/731; A61K 47/38; A61K 8/042

See application file for complete search history.

(56) References Cited

U.S. PATENT DOCUMENTS

| 6,201,072 B1 | 3/2001 | Rathi et al. |
| 2013/0116190 A1* | 5/2013 | Pollock ................. A61K 38/39 514/17.2 |

FOREIGN PATENT DOCUMENTS

| KR | 10-0750287 B1 | 8/2007 |
| KR | 10-2010-0067909 A | 6/2010 |

OTHER PUBLICATIONS

Miyazaki et al., "Biomineralization on chemically synthesized collagen containing immobilized poly-γ-glutamic acid", Dental Materials Journal 2013; 32(4): 544-549.*

Huang et al., "Development of fibroblast culture in three-dimensional activated carbon fiber-based scaffold for wound healing", J Mater Sci: Mater Med (2012) 23:1465-1478. DOI 10.1007/s10856-012-4608-4.*

* cited by examiner

*Primary Examiner* — Suzanne Marie Noakes
(74) *Attorney, Agent, or Firm* — NSIP Law

(57) ABSTRACT

A thermosensitive ionic composite having a multistage phase transition characteristic, a method for preparing the thermosensitive ionic composite, and a biodegradable composition containing the thermosensitive ionic composite are provided.

10 Claims, 9 Drawing Sheets

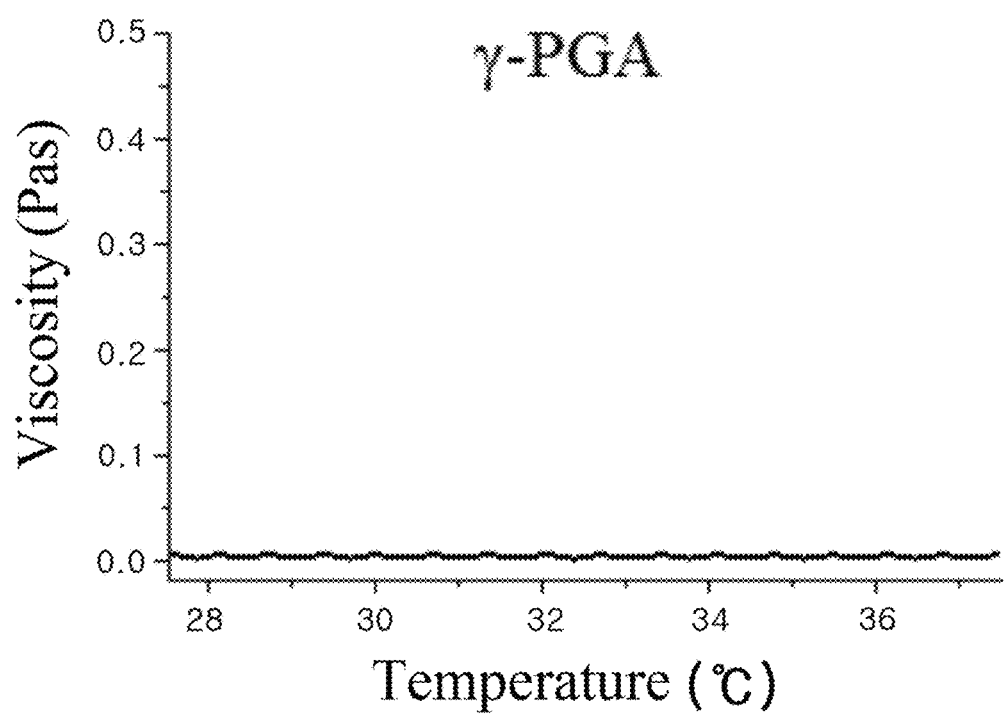

25°C

37°C

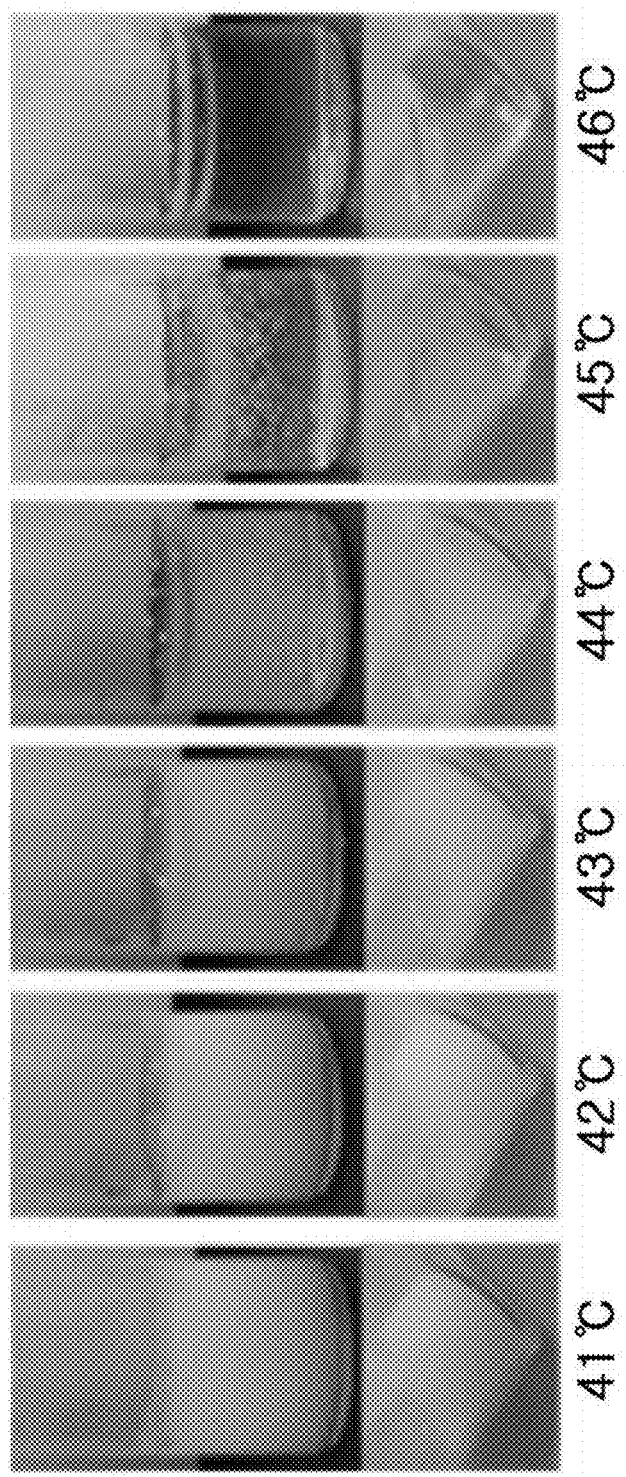

THERMOSENSITIVE IONIC COMPOSITE, PREPARING METHOD THEREOF, AND BIODEGRADABLE COMPOSITION CONTAINING THE SAME

CROSS-REFERENCE TO RELATED APPLICATION

This application claims the benefit of Korean Patent Application No. 10-2014-0107045 filed on Aug. 18, 2014 in the Korean Intellectual Property Office, the entire disclosure of which is incorporated herein by reference for all purposes.

TECHNICAL FIELD

The embodiments described herein pertain generally to a thermosensitive ionic composite, a method for preparing the thermosensitive ionic composite, and a biodegradable composition containing the thermosensitive ionic composite.

BACKGROUND

Since a hydrogel has a three-dimensional network structure in an aqueous solution via chemical crosslinkage or physical bond, it has been used as various medical materials. Especially, a thermosensitive hydrogel is characterized in that while an aqueous solution thereof is maintained in the liquid state at a low temperature, it changes into a gel with increase of a temperature. This sol-gel behavior can also be reversibly observed. Due to this characteristic, once the thermosensitive hydrogel is easily injected into a proper part, a gel with a three-dimensional structure is rapidly formed by the body temperature, and thus, the thermosensitive hydrogel has been evaluated to be greatly useful as an injection-type biomaterial such as a carrier of a bioactive substance like drug [Nature, 388, 860 (1997); U.S. Pat. No. 6,201,072].

However, the method for producing a polymer hydrogel through physical crosslinkage is disadvantageous since it is difficult to adjust the gelation behavior or the formation method. In addition, the method for forming a polymer hydrogel through chemical crosslinkage has a limit in the use for an injection-type biomaterial since it takes long time to form a gel [Biomaterials 24, 11 (2003); Biomaterials 26, 4495 (2005)]. Moreover, since most thermosensitive hydrogels that have been reported until the present have a single-point phase transition characteristic, whereby sol-gel transition occurs in the body temperature state, there have been many limitations in various applications thereof. Further, the thermosensitive hydrogels have a limit since they are synthetic materials. While the thermosensitive hydrogels have excellent performance and various superior properties, it is necessary to determine bioequivalence of the synthetic materials and newly start clinical trial stages for actual in vivo application. That is, it is difficult to immediately apply the thermosensitive hydrogels to the medical field, and significant time and funds for commercialization need to be invested. Accordingly, development of a hydrogel material, which has superior material properties and can be used immediately for in vivo application, is demanded.

SUMMARY

In view of the foregoing, embodiments provide a thermosensitive ionic composite, a method for producing the thermosensitive ionic composite, and a biodegradable composition containing the thermosensitive ionic composite.

However, the problems sought to be solved by the present disclosure are not limited to the above description, and other problems can be clearly understood by those skilled in the art from the following description.

A first aspect of embodiments provides a thermosensitive ionic composite including a collagen-based material or a gelatin-based material; and a negative charged polymer.

A second aspect of embodiments provides a producing method of a thermosensitive ionic composite, which includes mixing a collagen-based material or gelatin-based material with a negative charged polymer to form the composite.

A third aspect of embodiments provides a biodegradable composition, which includes the thermosensitive ionic composite in accordance with the first aspect of the embodiments.

A fourth aspect of embodiments provides a vaccine or antitumoral composition, which includes the biodegradable composition in accordance with the third aspect of the embodiments.

A fifth aspect of embodiments provides a tissue-engineered biomaterial or a dental material, which includes the biodegradable composition in accordance with the third aspect of the embodiments.

A sixth aspect of embodiments provides a skin external composition, which includes the biodegradable composition in accordance with the third aspect of the embodiments.

In accordance with the embodiments, it is possible to produce an advanced concept thermosensitive ionic composite, which has excellent biodegradability and thermosensitivity and a multistage phase transition characteristic, based on a bioapplicable material. After the ionic composite is formed by mixing collagen, gelatin or a purified collagen derivative having a structural characteristic, which induces a structure transformation (denaturation) phenomenon resulting from a hydrogen bond as a non-covalent bond and heat, with a negative charged polymer, and using electrostatic attraction, an advanced concept hydrogel, which exhibits a multistage phase transition characteristic, together with variation of the characteristic of the collagen-based material or gelatin-based material exhibiting the structure transformation according to a temperature, can be formed.

Especially, embodiments have developed an advanced concept thermosensitive ionic composite, which has the multistage phase transition characteristic, by using two (2) types of polymer materials with high biocompatibility without using any chemical crosslinkage or synthetic material, so that a source material of a hydrogel containing a useful component is produced at a room temperature, a hydrogel lacking a flow characteristic due to the thermosensitive characteristic is formed at the body temperature, and a release behavior of the useful component can be intelligently adjusted by an additional stimulus like constant increase of a temperature.

BRIEF DESCRIPTION OF THE DRAWINGS

FIG. 2A to FIG. 2C are graphs showing viscosity variation according to a temperature for I-type collagen, poly-γ-glutamic acid, and the thermosensitive ionic composite produced in accordance with an Example.

FIG. 5 shows a phase transition shape of the thermosensitive ionic composite in accordance with an Example at a temperature exceeding 40° C.

DETAILED DESCRIPTION

Figure 1:
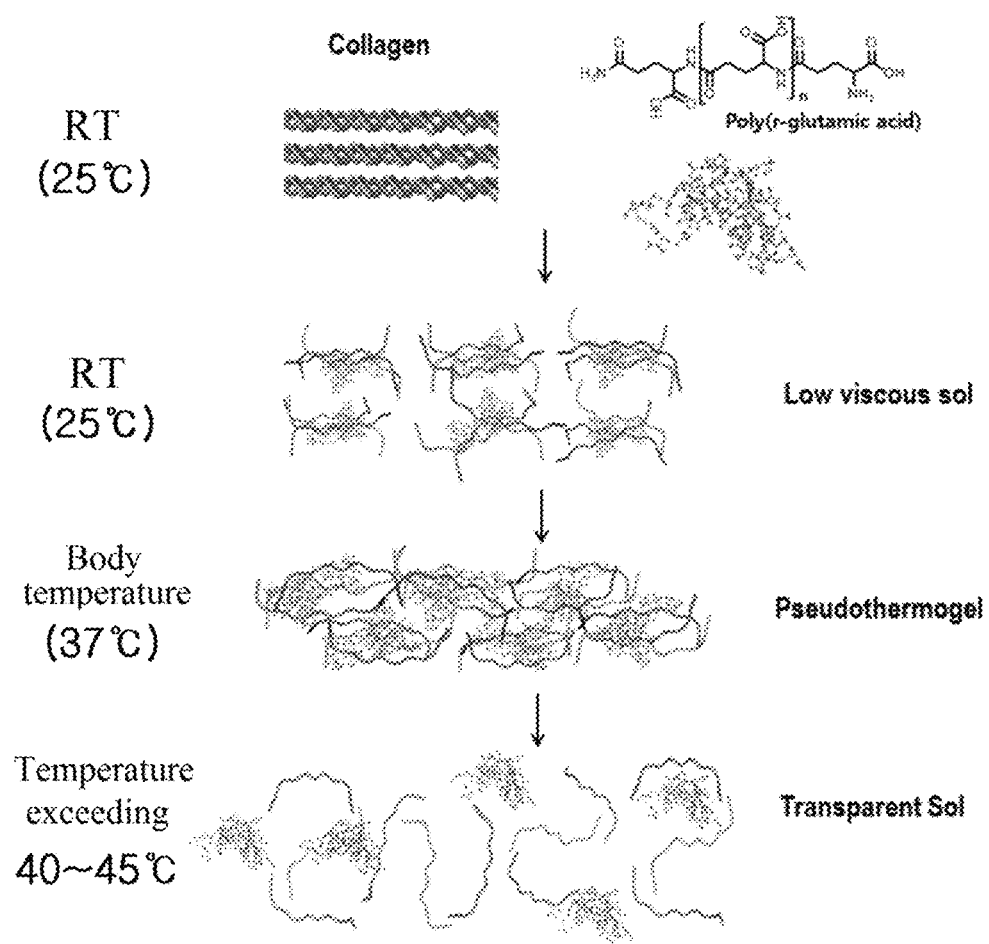
FIG. 1 is a schematic diagram showing a producing process of a thermosensitive ionic composite and a behavior characteristic of the thermosensitive ionic composite according to a temperature in accordance with an embodiment.

Hereinafter, embodiments will be described in detail with reference to the accompanying drawings so that inventive concept may be readily implemented by those skilled in the art. However, it is to be noted that the present disclosure is not limited to the embodiments but can be realized in various other ways. In the drawings, certain parts not directly relevant to the description are omitted to enhance the clarity of the drawings, and like reference numerals denote like parts throughout the whole document.

Throughout the whole document, the terms "connected to" or "coupled to" are used to designate a connection or coupling of one element to another element and include both a case where an element is "directly connected or coupled to" another element and a case where an element is "electronically connected or coupled to" another element via still another element.

Throughout the whole document, the term "on" that is used to designate a position of one element with respect to another element includes both a case that the one element is adjacent to the another element and a case that any other element exists between these two elements.

Throughout the whole document, the term "comprises or includes" and/or "comprising or including" used in the document means that one or more other components, steps, operations, and/or the existence or addition of elements are not excluded in addition to the described components, steps, operations and/or elements.

Throughout the whole document, the terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party.

Throughout the whole document, the term "step of" does not mean "step for."

Throughout the whole document, the term "combination of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Throughout the whole document, the description "A and/or B" means "A or B, or A and B."

Embodiments have been described in detail, but the present disclosure may not be limited to the embodiments.

The first aspect of the embodiments provides a thermosensitive ionic composite including a collagen-based material or gelatin-based material; and a negative charged polymer.

In an embodiment, the collagen-based material or gelatin-based material may be connected with the negative charged polymer via intermolecular non-covalent bond, but the present disclosure may not be limited thereto.

The collagen-based material has a steric structure (a hyper-structure, a triple-helix structure) due to its property, and the steric structure changes with increase of a temperature to gradually change into a simple random coil structure. However, when the collagen-based material or gelatin-based material (a random coil form where the triple helix structure of the collagen is loosened) is mixed with a negative charged polymer having a negative charge at a room temperature, a positive charged functional group exposed in the structure of the collagen or the gelatin and a negative charged functional group of the negative charged polymer are bound to each other, so that an ionic composite in the opaque state is formed by electrostatic attraction.

In an embodiment, the thermosensitive ionic composite may have a multistage phase transition characteristic according to change of a temperature, but not be limited thereto.

The thermosensitive ionic composite in accordance with the embodiments may have the multistage phase transition characteristic without requiring a chemical crosslinking process or including an additional synthetic material, and if the thermosensitive ionic composite to be used as a drug delivery contains a specific effective component, a release behavior of the effective component may be intelligently adjusted by using the multistage phase transition characteristic through an additional stimulus like constant increase of a temperature.

In an embodiment, the collagen-based material may include collagen or a purified collagen derivative, but not be limited thereto. The purified collagen derivative may include a member selected from the group consisting of I-type collagen, II-type collagen, III-type collagen, IV-type collagen and derivatives thereof, but not be limited thereto.

In an embodiment, the negative charged polymer may include a carboxyl or hydroxyl group, but not be limited thereto.

In an embodiment, the negative charged polymer may include a member selected from the group consisting of poly-γ-glutamic acid, hyaluronic acid, cellulose, polyacrylic acid, polyamino acid, derivatives thereof, and combinations thereof, but not be limited thereto.

In an embodiment, with respect to the multistage phase transition characteristic, the thermosensitive ionic composite exists in the sol state at a temperature less than the body temperature; undergoes phase transition to be in the hydrogel state at the body temperature; and undergoes phase transition to be in the sol state at a temperature exceeding 40° C.

In an embodiment, the hydrogel may include a three-dimensional structure formed by connecting the collagen-based material or gelatin-based material with the negative charged polymer via intermolecular non-covalent crosslinking bond.

The solution of the collagen-based material or gelatin-based material, which exhibits a similar behavior to that of a gel and a high viscosity property at a room temperature, undergoes rapid decrease of viscosity with addition of the negative charged polymer, and thereby, having a superior flow characteristic. Further, when the temperature changes into the body temperature, an advanced concept hydrogel having a three-dimensional structure is formed by combination of the hydrogen bond and the structure transformation of the collagen and the above-mentioned electrostatic attraction. In addition, as the temperature increases from the body temperature up to a temperature exceeding 40° C., the three-dimensional structure is eventually destroyed due to further structure transformation of the collagen-based material or gelatin-based material, so that the hydrogel changes into the transparent sol state.

In an embodiment, the viscosity of the hydrogel may be from about 0.1 Pas to 5 Pas, but not be limited thereto. The viscosity of the hydrogel (pseudothermogel) may be from about 0.1 Pas to about 5 Pas, from about 0.1 Pas to about 3 Pas, from about 0.1 Pas to about 1 Pas, from about 0.1 Pas to about 0.5 Pas, from about 0.5 Pas to about 5 Pas, from about 1 Pas to about 5 Pas or from about 3 Pas to about 5 Pas, but not be limited thereto.

In an embodiment, a weight ratio of the collagen-based material or gelatin-based material and the negative charged polymer may be from 1 to 4:1, but not be limited thereto. With respect to 1 part by weight of the negative charged polymer, the collagen-based material or gelatin-based material may be mixed at from about 1 part by weight to about 4 parts by weight, from about 1 part by weight to about 3 parts by weight, from about 1 part by weight to about 2 parts by weight, from about 1 part by weight to about 1.5 parts by weight, from about 1.5 to about 4 parts by weight, from about 2 parts by weight to about 4 parts by weight, or from about 3 parts by weight to about 4 parts by weight, but not be limited thereto.

FIG. 1 shows a process, in which the collagen and the negative charged polymer (e.g., poly-γ-glutamic acid) form an ionic bond at a room temperature so as to form the thermosensitive ionic composite. As shown in FIG. 1, when the collagen is mixed with poly-γ-glutamic acid at a room temperature, the non-covalent bond based on the hydrogen bond of the collagen is loosened, and in this case, the positive charged functional group of the collagen and the negative charged functional group of the negative charged polymer interact with each other so as to produce a low viscous sol having a loose structure. When the temperature increases to reach a temperature around the body temperature, more positive charged functional groups of the collagen are exposed, and the collagen undergoes structure transformation (denaturation) to have a random coil form. In this case, the negative charged polymer serves as a crosslinking agent for connecting the loosened chains of the collagen-based material or gelatin-based material to one another, so as to produce a hydrogel (pseudothermogel) having a steric structure, in which the hydrogen bond force of the collagen-based material or gelatin-based material and the ionic bond force between the collagen-based material or gelatin-based material and the negative charged polymer are mutually complementary. When the temperature further increases to exceed 40° C., the structure of the collagen-based material or gelatin-based material is eventually completely destroyed, so that the interaction between the collagen-based material or gelatin-based material and the negative charged polymer is reduced, and the three-dimensional structure also changes into the transparent sol state.

The second aspect of the embodiments provides a method for preparing a thermosensitive ionic composite, which includes mixing the collagen-based material or gelatin-based material with the negative charged polymer to form the composite.

In an embodiment, the collagen-based material or gelatin-based material may be connected with the negative charged polymer via intermolecular non-covalent bond, but the present disclosure may not be limited thereto.

In an embodiment, the collagen-based material may include collagen or a purified collagen derivative, but not be limited thereto. The purified collagen derivative may include a member selected from the group consisting of I-type collagen, II-type collagen, III-type collagen, IV-type collagen and derivatives thereof, but not be limited thereto.

In an embodiment, the negative charged polymer may contain a carboxyl group or a hydroxyl group, but not be limited thereto.

In an embodiment, the negative charged polymer may include a member selected from the group consisting of poly-γ-glutamic acid, hyaluronic acid, cellulose, polyacrylic acid, polyamino acid, derivatives thereof, and combinations thereof, but not be limited thereto.

In an embodiment, the thermosensitive ionic composite may include hydrogel, and the hydrogel may have a three-dimensional structure formed by connecting the collagen-based material or gelatin-based material with the negative charged polymer via intermolecular non-covalent crosslinking bond, but not be limited thereto. The hydrogel may be a result of phase transition of the thermosensitive ionic composite by the body temperature.

In an embodiment, the viscosity of the hydrogel may be from about 0.1 Pas to about 5 Pas, but not be limited thereto. The viscosity of the hydrogel (pseudothermogel) may be from about 0.1 Pas to about 5 Pas, from about 0.1 Pas to about 3 Pas, from about 0.1 Pas to about 1 Pas, from about 0.1 Pas to about 0.5 Pas, from about 0.5 Pas to about 5 Pas, from about 1 Pas to about 5 Pas or from about 3 Pas to about 5 Pas, but not be limited thereto.

In an embodiment, in forming the composite, the collagen-based material or gelatin-based material may be mixed with the negative charged polymer at a weight ratio of about 1 to about 4:1, but not be limited thereto. With respect to 1 part by weight of the negative charged polymer, the collagen-based material or gelatin-based material may be mixed at from about 1 part by weight to about 4 parts by weight, from about 1 part by weight to about 3 parts by weight, from about 1 part by weight to about 2 parts by weight, from about 1 part by weight to about 1.5 parts by weight, from about 1.5 to about 4 parts by weight, from about 2 parts by weight to about 4 parts by weight, or from about 3 parts by weight to about 4 parts by weight, but not be limited thereto.

The third aspect of the embodiments provides a biodegradable composition, which includes the thermosensitive ionic composite in accordance with the first aspect of the embodiments.

Since the mixture of the collagen-based material or gelatin-based material and the negative charged polymer, which is contained in the biodegradable composition in accordance with the embodiments, may not only exhibit a sol-gel behavior through non-covalent bond like electrostatic attraction, but also have thermosensitivity resulting in the multi-stage phase transition characteristic according to the body temperature and further change of a temperature, it is advantageous in that it is possible to easily envelope a variety of drug by using the characteristic of change into a gel according to change of a temperature; it is possible to apply the mixture to various drug delivery systems by using the flow characteristic induced by the phase transition under a temperature condition for a desired purpose and a sustained release phenomenon; and furthermore, it is possible to use the mixture for various fillers and cartilages, and tissue-engineered biomaterials or dental materials, in addition to vaccines or antitumoral compositions, or pharmaceutical or cosmetic adjuvants. Further, since the biodegradable composition in accordance with the embodiments is easily naturally dissolved and hydrolyzed in the human body after lapse of certain time and has biocompatibility, it is advantageous in that it does not require an additional process for removing the composition after the composition is introduced into the human body to be used as a drug delivery, a tissue-engineered biomaterial, a dental material or others.

Further, the biodegradable composition in accordance with the embodiments may be used for production of a skin external composition for a therapy or beauty purpose by sealing drug or a beauty ointment therein, and when the skin external composition, in which drug or a beauty ointment is sealed, is spread on the skin or the like, the composition enables the drug or beauty ointment to be quickly and evenly delivered to the inside of the skin at a certain temperature.

The fourth aspect of the embodiments provides a vaccine or antitumoral composition, which includes the biodegradable composition in accordance with the third aspect of the embodiments.

The fifth aspect of the embodiments provides a tissue-engineered biomaterial or a dental material, which includes the biodegradable composition in accordance with the third aspect of the embodiments.

The sixth aspect of the embodiments provides a skin external composition, which includes the biodegradable composition in accordance with the third aspect of the embodiments.

Although the detailed descriptions of the third to sixth aspects of the embodiments, which overlap with those of the first or second aspect of the embodiments, have been omitted, the descriptions of the first or second aspect of the embodiments may be identically applied to the third aspect of the embodiments even though they are omitted in the description of the third aspect of the embodiments.

Hereinafter, the embodiments are described more in detail by using Examples, but the Examples are intended merely to facilitate understanding of the present disclosure, and the present disclosure is not limited to the Examples.

EXAMPLES

Example 1: Preparation of an Ionic Composite Using Collagen and Poly-γ-Glutamic Acid I-type collagen (Bioland Corporation, Cheonan, South Korea, 2~5 KDa) was dissolved in a phosphate buffer solution at a concentration of 2%, and poly-γ-glutamic acid (γ-PGA; Bioleaders Corporation, Daejeon, South Korea) was completely dissolved in a common aqueous solution at a room temperature for sufficient time. When the two solutions were prepared, sterilization prior to use was performed by using a 0.22 μm filter. The collagen-containing solution and the poly-γ-glutamic acid-containing solution were mixed with each other at a mixture ratio of 4:1, and strongly stirred by using a stirrer so that an ionic composite of collagen and poly-γ-glutamic acid was prepared. Variation of viscosity of the obtained ionic composite was observed by gradually increasing the temperature of the ionic composite, and FIG. 2C provides the results.

Figure 2A:
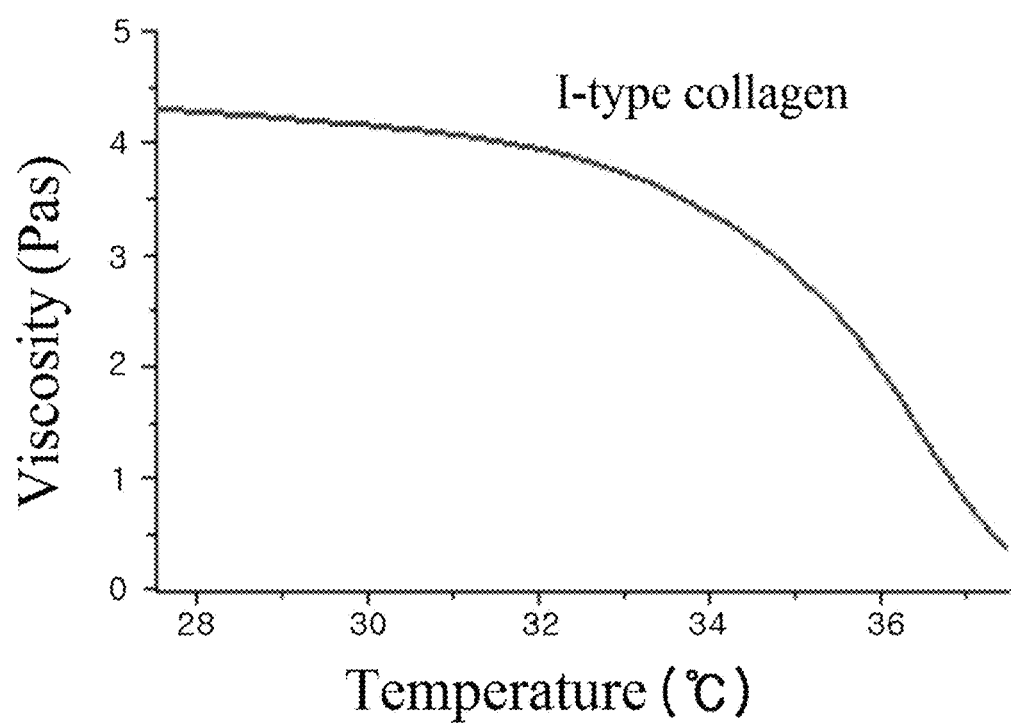
Figure 2C:
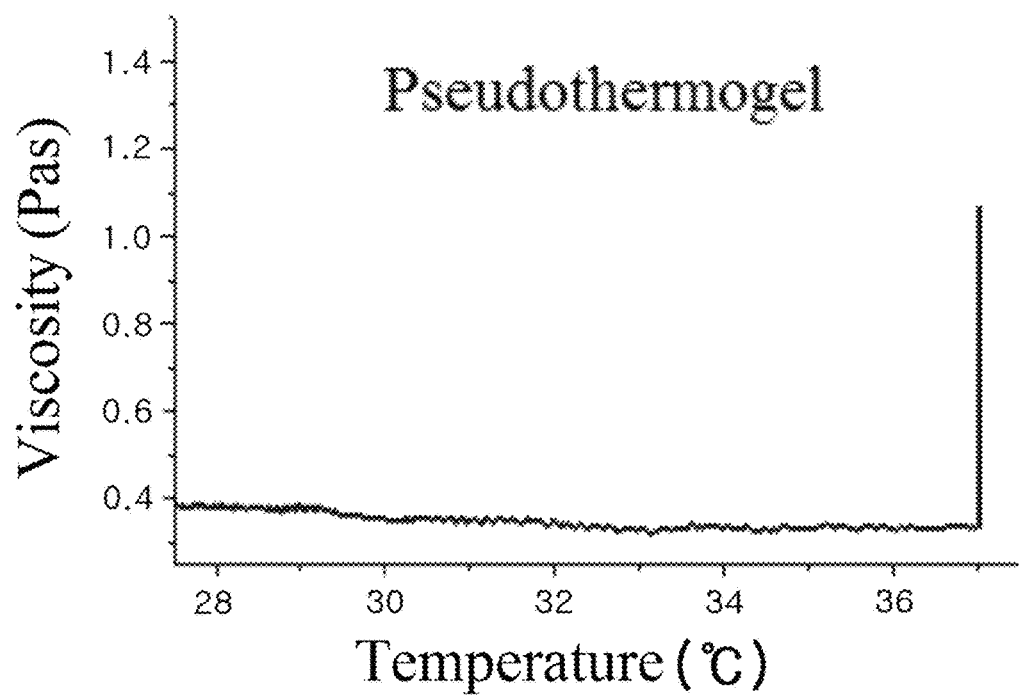

FIG. 2A to FIG. 2C are graphs showing variation of viscosity according to a temperature with regard to I-type collagen, poly-γ-glutamic acid, and the thermosensitive ionic composite prepared according to Example 1. While the viscosity of the collagen tended to have been gradually reduced due to structure transformation as the temperature increases (refer to FIG. 2A), the viscosity of the poly-γ-glutamic acid exhibited little change (refer to FIG. 2B). However, as shown in FIG. 2C, it was observed that the viscosity of the ionic composite according to Example 1 showed little change at a temperature less than 37° C. and rapidly increased around the body temperature [Pseudothermogel was formed].

Figure 3A:
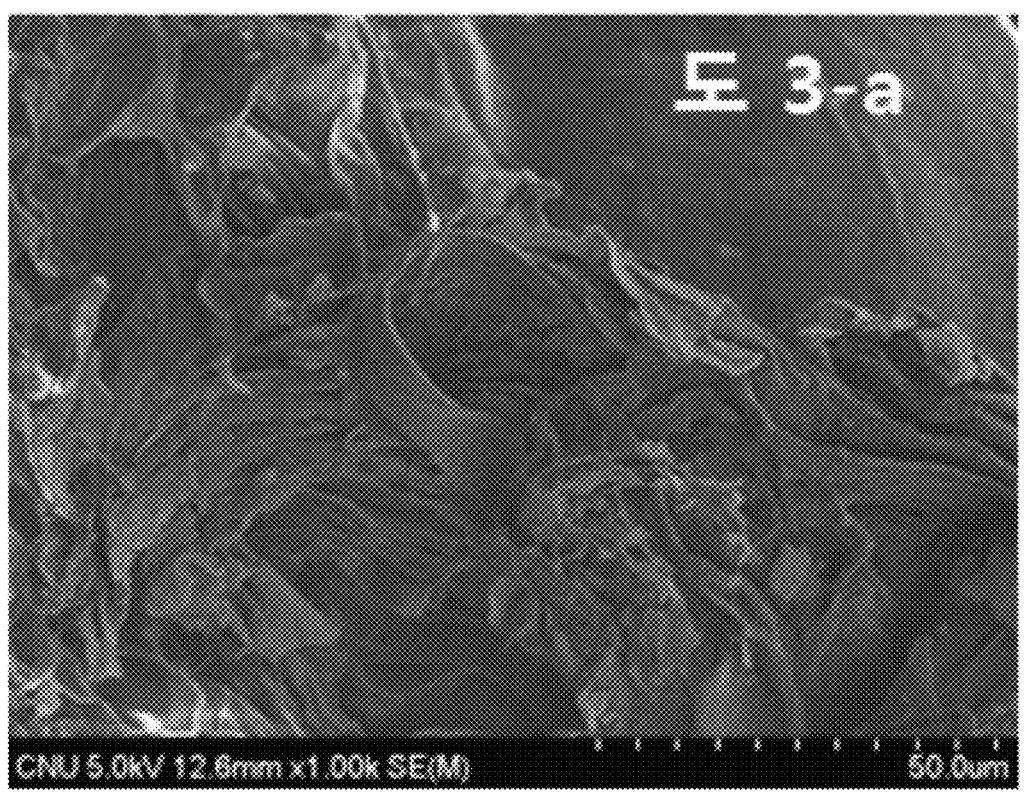
FIG. 3A to FIG. 3C are scanning electron microscope images of collagen at a room temperature and the thermosensitive ionic composite in accordance with an Example at 25° C. and 37° C.
Figure 3B:
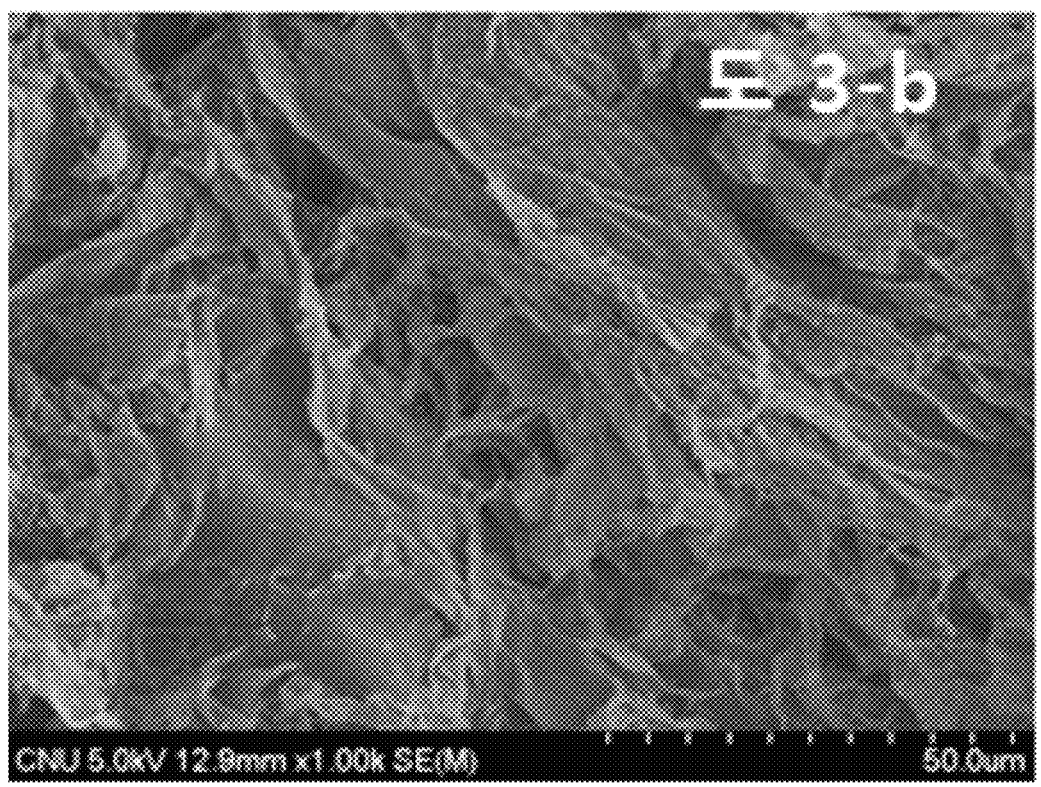
Figure 3C:
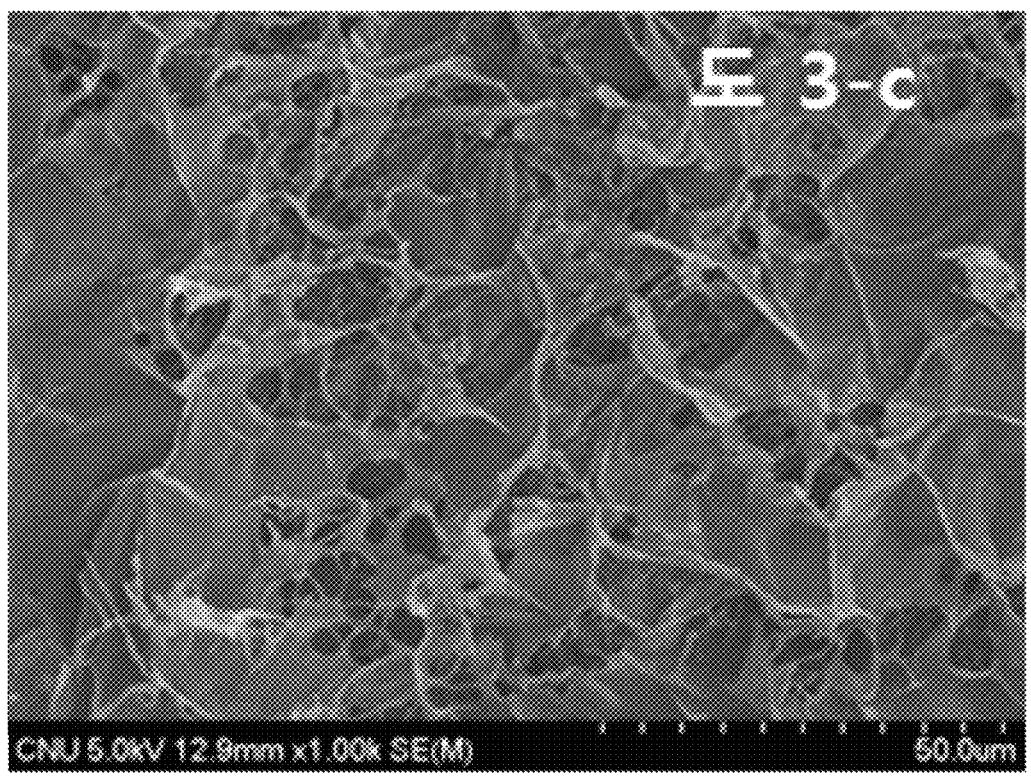

The obtained ionic composite was observed by using a scanning electron microscope while differently adjusting the temperature, and FIG. 3B and FIG. 3C provide the results.

FIG. 3A and FIG. 3C are scanning electron microscope images of the collagen at a room temperature and the thermosensitive ionic composite according to Example 1 at 25° C. and 37° C. It was identified that the collagen existed in a bundle form at a room temperature (FIG. 3A), the bundle was mostly loosened (FIG. 3B) when the ionic composite was formed by the collagen and the poly-γ-glutamic acid, and a three-dimensional network structure was formed around 37° C. (FIG. 3C).

Accordingly, from the results of FIG. 2A to FIG. 2C and FIG. 3A to FIG. 3C, it was observed that the material existing in the sol sate at a room temperature changed into the gel state around the body temperature.

Figure 4:
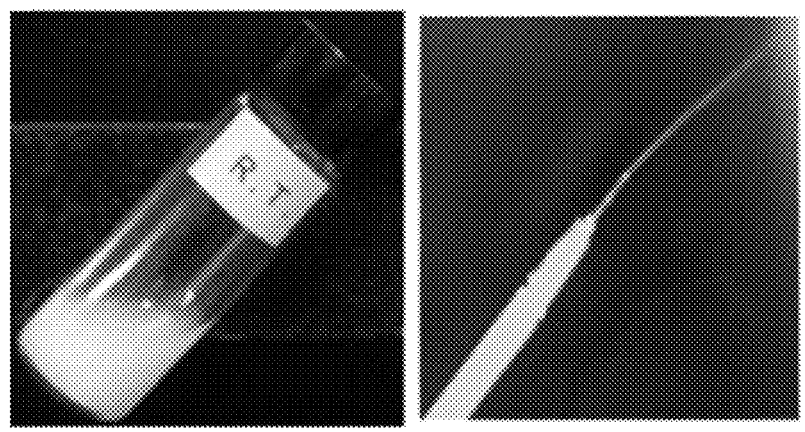
FIG. 4 shows a shape and a flow characteristic of the thermosensitive ionic composite in accordance with an Example at 25° C. and 37° C.
Figure 4:
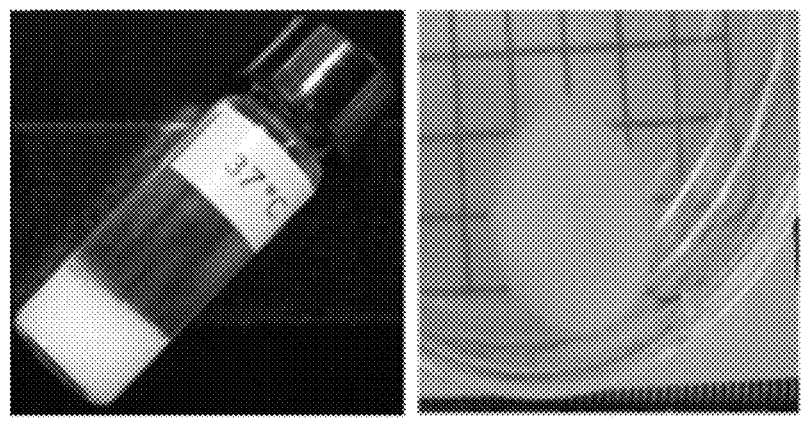

The shape and the flow characteristic of the obtained ionic composite were observed by differently adjusting the temperature, and FIG. 4 provides the results.

FIG. 4 shows the shape and the flow characteristic of the thermosensitive ionic composite according to Example 1 at 25° C. and 37° C. As shown in FIG. 4, the ionic composite, which actually exhibited the flow characteristic at a room temperature, changed into the gel state lacking the flow characteristic at 37° C.

The obtained ionic composite was heated to a temperature exceeding 40° C. to observe the phase transition form thereof, and FIG. 5 provides the results.

FIG. 5 shows a phase transition form of the thermosensitive ionic composite according to Example 1 at a temperature exceeding 40° C. As shown in FIG. 5, once the temperature increases to 37° C. or more, the structure of the ionic composite in the gel state gradually becomes loose, undergoes phase transition to be in the opaque sol state around 41° C. to 43° C., and further undergoes phase transition to be in the transparent sol state around 44° C. to 46° C.

Example 2: Preparation of an Ionic Composite Using Collagen and Hyaluronic Acid

A collagen-containing solution and a hyaluronic acid-containing solution (Bioland Corporation, Cheonan, South Korea, 500-1300 KDa) were prepared by the same process as that used in Example 1. The collagen-containing solution and the hyaluronic acid-containing solution were mixed with each other at a mixture ratio of 4:1, and strongly stirred by using a stirrer so that an ionic composite of the collagen and the hyaluronic acid was prepared. The process for preparing the samples and the process for characterizing the materials are based on those in Example 1.

Example 3: Preparation of an Ionic Composite Using Collagen and Cellulose

A collagen-containing solution and a cellulose-containing solution (Sodium Carboxy Methyl Cellulose, Sigma-Aldrich, 90 KDa) were prepared by the same process as that used in Example 1. The collagen-containing solution and the hyaluronic acid-containing solution were mixed with each other at a mixture ratio of 4:1, and strongly stirred by using a stirrer so that an ionic composite of the collagen and the cellulose was prepared. The process for preparing the samples and the process for characterizing the materials are based on those in Example 1.

Most conventional thermosensitive hydrogels, which exhibit the sol-gel behavior, are synthetic materials, and are disadvantageous in that they have overly low dissolubility, which cannot be controlled. On the other hand, in case of the thermosensitive ionic composite according to the embodiments, the dissolubility and the sustained release strength can be easily adjusted according to types and a mixture ratio of the collagen-based material or gelatin-based material and the negative charged polymer, so that the thermosensitive ionic composite can be used for various fillers and cartilages, and tissue-engineered biomaterials or dental materials, in addition to injection adjuvants.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

What is claimed is:

1. A thermosensitive ionic composite, comprising:
   a collagen-based material; and
   a negative charged polymer,
   wherein the negative charged polymer comprises a member selected from the group consisting of: poly-γ-glutamic acid, cellulose, derivatives thereof, and combinations thereof,
   wherein the thermosensitive ionic composite has a multistage phase transition characteristic depending upon a temperature variation,
   wherein the multistage phase transition characteristic includes the thermosensitive ionic composite existing in a sol state at a temperature below body temperature, undergoing phase-transition to be in a hydrogel state at body temperature, and undergoing phase transition to be in a sol state at a temperature exceeding 40° C., and
   wherein the hydrogel includes a 3-dimensional structural body formed by connecting the collagen-based material with the negative charged polymer via non-covalent binding between molecules.

2. The thermosensitive ionic composite of claim 1, wherein the collagen-based material is connected with the negative charged polymer via intermolecular non-covalent binding.

3. The thermosensitive ionic composite of claim 1, wherein the collagen-based material comprises a collagen or a purified collagen derivative.

4. The thermosensitive ionic composite of claim 1, wherein a weight ratio of the collagen-based material and the negative charged polymer is 1 to 4:1.

5. A biodegradable composition, comprising the thermosensitive ionic composite of claim 1.

6. A vaccine or an antitumoral composition, comprising the biodegradable composition of claim 5.

7. A tissue-engineered biomaterial or a dental material, comprising the biodegradable composition of claim 5.

8. A skin external composition, comprising the biodegradable composition of claim 5.

9. The thermosensitive ionic composition of claim 1, wherein
   the collagen-based material comprises I-type collagen,
   the I-type collagen is dissolved in a phosphate buffer solution at a concentration of 2%,
   the negative charged polymer comprises poly-γ-glutamic acid, and
   a weight ratio of the collagen-based material and the negative charged polymer is 4:1.

10. The thermosensitive ionic composition of claim 1, wherein
    the negative charged polymer comprises carboxy methyl cellulose, and
    a weight ratio of the collagen-based material and the negative charged polymer is 4:1.

* * * * *